US008945634B2

(12) United States Patent
Antony

(10) Patent No.: US 8,945,634 B2
(45) Date of Patent: *Feb. 3, 2015

(54) COMPOSITION TO ENHANCE HDL CHOLESTEROL AND TO DECREASE INTIMA-MEDIA THICKENING IN ANIMALS AND HUMANS AND A METHOD FOR ITS PREPARATION

(71) Applicant: Benny Antony, Ankamaly (IN)

(72) Inventor: Benny Antony, Ankamaly (IN)

(73) Assignee: Arjuna Natural Extracts, Ltd., Alwaye (IN)

( * ) Notice: Subject to any disclaimer, the term of this patent is extended or adjusted under 35 U.S.C. 154(b) by 24 days.

This patent is subject to a terminal disclaimer.

(21) Appl. No.: 13/886,287

(22) Filed: May 3, 2013

(65) Prior Publication Data

US 2013/0309339 A1 Nov. 21, 2013

Related U.S. Application Data

(60) Division of application No. 13/374,931, filed on Jan. 24, 2012, now Pat. No. 8,455,020, which is a division of application No. 12/805,191, filed on Jul. 16, 2010, now Pat. No. 8,158,167, which is a division of application No. 11/643,788, filed on Dec. 22, 2006, now Pat. No. 7,780,996, which is a continuation-in-part of application No. 11/111,798, filed on Apr. 22, 2005, now abandoned, which is a continuation of application No. PCT/IN03/00137, filed on Apr. 3, 2003.

(30) Foreign Application Priority Data

Mar. 3, 2003 (IN) ................................ 169/MAS/03

(51) Int. Cl.
*A61K 36/00* (2006.01)

(52) U.S. Cl.
USPC ........................................................ 424/725

(58) Field of Classification Search
None
See application file for complete search history.

(56) References Cited

U.S. PATENT DOCUMENTS

| 6,124,268 | A | 9/2000 | Ghosal |
| 6,235,721 | B1 | 5/2001 | Ghosal |
| 6,290,996 | B1 | 9/2001 | Ghosal |
| 6,362,167 | B1 | 3/2002 | Ghosal |
| 7,001,619 | B2 | 2/2006 | Johri et al. |
| 7,780,996 | B2 * | 8/2010 | Antony ................ 424/725 |
| 2003/0008048 | A1 | 1/2003 | Winston et al. |
| 2003/0194452 | A1 | 10/2003 | Agarwal et al. |

FOREIGN PATENT DOCUMENTS

| WO | WO 96/24327 A | 8/1996 |
| WO | WO 02/23995 A | 3/2002 |

OTHER PUBLICATIONS

Ghosal, S, Tripathi, VK and Chauhan S, Active Constituents of *Emblica officinalis*: Part 1—The Chemistry and Antioxidative Effects of Two New Hydrolysable Tannins, Emblicanin A and B, Indian Journal of Chemistry, 35B: 941-948 (1996).
Anila, L, and Vijayalakshmi, NR, Flavonoids from *Emblica officinalis* and *Mangifera indica*—Effectiveness for Dyslipedemia, Journal of Ethnopharmacology, 79: 81-87 (2002).
Brewer, HB, High-Density Lipoproteins: A New Potential Therapeutic Target for the Prevention of Cardiovascular Disease, Arterioscler. Thromb. Vasc. Biol., 24: 387-391 (2004).
Brewer, HB, Increasing HDL Cholesterol Levels, N. Engl. J. Med., 350 (15): 1491-1494 (2004), Massachusetts Medical Society.
Furberg, CD, Adams, HP, Applegate, WB, Byington, RP, Espeland, MA, Hartwell, T, Hunninghake, DB, Lefkowitz, DS, Probstfield, J, and Riley, WA, Effect of Lovastatin on Early Carotid Artherosclerosis and Cardiovascular Events. Asymptomatic Carotid Artery Progression Study (ACAPS) Research Group, Circulation, 90: 1679-1687 (1994), American Heart Asociation.
Navab, M, Anantharamaiah, GM, Hama, S, Garber, DW, Chaddha, M, Hough, G, Lallone, R, and Fogelman, A, Oral Administration of an Apo A-1 Mimetic Peptide Synthesized From D-Amino Acids Dramatically Reduces Atherosclerosis in Mice Independent of Plasma Cholesterol, Circulation, 105: 290-292 (2002), American Heart Association.
Grundy, S, Statin Trials and Goals of Cholesterol-Lowering Therapy, Circulation, 97: 1436-1439 (1998), American Heart Association.
Ridker, PM, Clinical Application of C-Reactive Protein for Cardiovascular Disease Detection and Prevention, Circulation, 107: 363-369 (2003), American Heart Association.
Ridker, P, Cannon, CP, Morrow, D, Rifai, N, Rose, LM, McCabe, CH, Pfeffer, MA, and Braunwald, E, C-Reactive Protein Levels and Outcomes after Statin Therapy, N. Engl. J. Med., 352:20-28 (2005), Massachusetts Medical Society.
Chew, DP, Bhatt, DL, Robbins, MA, Penn, MS, Schneider, JP, Lauer, MS, Topol, EJ, and Ellis, SG, Incremental Prognostic Value of Elevated Baseline C-Reactive Protein Among Established Markers of Risk in Percutaneous Coronary Intervention, Circulation, 104: 992-997 (2001), American Heart Association.
Haffner, SM, Lehto, S, Ronnemaa, T, Pyorala, K, and Laakso, M, Mortality from Coronary Heart Disease in Subjects with Type 2 Diabetes and in Nondiabetic Subjects With and Without Prior Myocardial Infarction, N. Engl. J. Med., 339 (4): 229-234 (1998), Massachusetts, Medical Society.

(Continued)

*Primary Examiner* — Terry A McKelvey
*Assistant Examiner* — Randall Winston
(74) *Attorney, Agent, or Firm* — Jyoti C Iyer

(57) ABSTRACT

A method of producing a product to correct hypercholesterolemia including pulping fruits of *Emblica officinalis* with demineralized water to create a slurry. The slurry is treated with pectinase. The pectinase-treated slurry is filtered to create a solution. The solution is concentrated to create a product. A product having an extract of *Emblica officinalis* for prophylactic and for therapeutic treatment of coronary diseases, atherosclerosis, hypothyroidism and hyperthyroidism.

2 Claims, 2 Drawing Sheets

(56) References Cited

OTHER PUBLICATIONS

Malmberg, K, Yusuf, S, Gerstein, HC, Brown, J, Zhao, F, Hunt, D, Piegas, L, Calvin, J, Keltai, M, Budaj, A, and for the OASIS Registry Investigators, Impact of Diabetes on Long-Term Prognosis in Patients with Unstable Angina and Non-Q-Wave Myocardial Infarction: Results of the OASIS (Organization to Assess Strategies for Ischemic Syndromes) Registry, Circulation, 102: 1014-1019 (2000), American Heart Association.

Sawin, CT, Geller, A, Wolf, PA, Belanger, AJ, Baker, E, Bachrach, P, Wilson, P, Benjamin, EJ, and D'Agostino RB, Low Serum Thyrotropin Concentrations as a Risk Factor for Atrial Fibrillation in Older Persons, N. Engl. J. Med., 331: 1249-1252 (1994).

Klein, I, and Ojamaa, K, Thyroid Hormone and the Cardiovascular System, N. Engl. J. Med., 344(7): 501-509 (2001), Massachusetts Medical Society.

Pasceri, V, Willerson, JT, and Yeh, ETH, Direct Proinflammatory Effect of C-Reactive Protein on Human Endothelial Cells, Circulation, 102: 2165-2168 (2000), American Heart Association.

Sacks, FM, Pfeffer, MA, Moye, LA, Rouleau, JL, Rutherford, JD, Cole, TG, Brown, L, Warnica, JW, Arnold, JMO, Wun, C-C, Davis, BR, and Braunwald, E, for the Cholesterol and Recurrent Events Trial Investigators, The Effect of Pravastatin on Coronary Events After Myocardial Infarction in Patients with Average Cholesterol Levels, N. Engl. J. Med., 335(14): 1001-1009 (1996), Massachusetts Medical Society.

Ross, R, Atherosclerosis—An Inflammatory Disease, N. Engl. J. Med., 340(2): 115-126 (1999), Massachusetts Medical Society.

Stefanick, ML, Mackey, S, Sheehan, M, Ellsworth, N, Haskell, WL, and Wood, PD, Effects of Diet aand Exercise in Men and Postmenopausal Women with Low Levels of HDL Cholesterol and High Levels of LDL Cholesterol, N. Engl. J. Med., 339(1): 12-20 (1998), Massachusetts Medical Society.

Pederson, TR, Olsson, AG, Faergeman, O, Kjekshus, J, Wedel, H, Berg, K, Wilhelmsen, L, Haghfelt, T, Thorgeirsson, G, Pyorala, K, Miettinen, T, Christophersen, B, Tobert, JA, Musliner, TA, Cook, TJ, for the Scandinavian Simvastatin Survival Study Group, Lipoprotein Changes and Reduction in the Incidence of Major Coronary Heart Disease Events in the Scandinavian Simvastatin Survival Study (4S), Circulation, 97: 1453-1460 (1998), American Heart Association.

Sacks, FM, Moye, LA, Davis, BR, Cole, TG, Rouleau, JL, Nash, DT, Pfeffer, MA, and Braunwald, E, Relationship Between Plasma LDL Concentrations During Treatment With Pravastatin and Recurrent Coronary Events in the Cholesterol and Recurrent Events Trial, Circulation, 97: 1446-1452 (1998), American Heart Association.

Ridker, PM, Rifai, N, Pfeffer, MA, Sacks, F, and Braunwald, E, Long-Term Effects of Pravastatin on Plasma Concentration of C-Reactive Protein, Circulation, 100:230-235 (1999), American Heart Association.

West of Scotland Coronary Prevention Study Group, Influence of Pravastatin and Plasma Lipids on Clinical Events in the West of Scotland Coronary Prevention Study (WOSCOPS), Circulation, 97: 1440-1445 (1998), American Heart Association.

Juonala, M, Viikari, JSA, Laitinen, T, Marniemi, J, Helenius, H, Ronnemaa, T, and Raitakari, OT, Interrelations Between Brachial Endothelial Function and Carotid Intima-Media Thickness in Young Adults: The Cardiovascular Risk in Young Finns Study, Circulation, 110: 2918-2923 (2004), American Heart Association.

Chen, Z, Fukutomi, T, Zago, AC, Ehlers, R, Detmers, PA, Wright, SD, Rogers, C, and Simon, DI, Simvastatin Reduces Neointimal Thickening in Low-Density Lipoprotein Receptor-Deficient Mice After Experimental Angioplasty Without Changing Plasma Lipids, Circulation, 106: 20-23 (2002), American Heart Association.

Sheperd, J, Cobbe, SM, Ford, I, Isles, CG, Lorimer, RA, Macfarlane, PW, McKillop, JH, and Packard, CJ, for the West of Scotland Coronary Prevention Study Group, Prevention of Coronary Heart Disease with Pravastatin in Men With Hypercholesterolmia, N. Engl. J. Med., 333(20): 1301-1307 (1995), Massachusetts Medical Scoiety.

Thakur, CP, Thakur, B, Singh, S, Sinha, PK, and, Sinha SK, The Ayurvedic medicines Haritaki, Amla and Bahira Reduce Cholesterol-Induced Atherosclerosis in Rabbits, Intl. J. Cardiology, 21: 167-175 (1988).

Thakur, CP, and Mandal, K, Effect of *Emblica officinalis* on Cholesterol-Induced Atherosclerosis in Rabbits, Indian J. Med. Res., 79: 142-146 (1984), Indian Council of Medical Research.

Sai Ram, M, Neetu, D, Deepti, P, Vandana, M, Ilavazhagan, G, Kumar, D, and Selvamurthy, W, Cytoprotective Activity of Amla (*Emblica officinalis*) Against Chromium (VI) Induced Oxidative Injury in Murine Macrophages, Phytother. Res., 17: 430-433 (2003), John Wiley & Sons, Ltd.

Nemmani, KVS, Jena, GB, Dey, CS, Kaul, CL, and, Ramarao, P, Cell Proliferation and Natural Killer Cell Activity by Polyherbal Formulation, Immu-21 in Mice, Indian Journal of Experimental Biology, 40: 282-287 (2002).

Panda, S, and Kar, A, Fruit Extract of *Emblica officinalis* Ameliorates Hyperthyroidism and Hepatic Lipid Peroxidation in Mice, Pharmazie, 58: 753-755 (2003).

Sabu, MC, and Kuttan, R, Anti-diabetic Activity of Medicinal Plants and its Relationship with their Antioxidant Property, J Ethnopharmacology, 81: 155-160 (2002).

Sai Ram, M, Neetu, D, Yogesh, B, Anju, B, Dipti, P, Pauline, T, Sharma, SK, Sarada, SKS, Ilavazhagan, G, Kumar, D, and Selvamurthy, W, Cyto-protective and Immunomodulation Properties of Amla (*Emblica officinalis*) on Lymphocytes: An In-Vitro Study, J Ethnopharmacology, 81:5-10 (2002).

Muruganandam, AV, Kumar, V, and Bhattacharya, SK, Effect of Poly Herbal Formulation, EuMil, on Chronic Stress-Induced Homeostatic Perturbations in Rats, Indian J Experimental Biology, 40: 1151-1160 (2002).

Babu, PS, and Prince, PSM, Antihyperglycaemic and Antioxidant Effect of Hyponidd, An Ayurvedic Herbomineral Formulation in Streptozotocin-Induced Diabetic Rats, J Pharmacy and Pharmacology, 56: 1435-1442 (2004).

Duan, W, Yu, Y, and Zhang, L, Antiatherogenic Effects of *Phyllanthus emblica* Associated with Corilagin and its Analogue, Yakugaku Zasshi, 125(7): 587-591 (2005), The Pharmaceutical Society of Japan.

Tariq, M, Hussain, SJ, Asif, M, and Jahan, M, Protective Effect of Fruit Extracts of *Emblica officinalis* (Gaertn.) & *Terminalia belerica* (Roxb.) in Experimental Myocardial Necrosis in Rats, Indian J. exp. Biol., 15(6): 485-486 (1977).

Mishra, M, Pathak, UN, and Khan, AB, *Emblica officinalis* Gaertn and Serum Cholesterol Level in Experimental Rabbits, Br. J. exp. Path., 62: 526-528 (1981).

Mathur, R, Sharma, A, Dixit, VP, and Varma, M, Hypolipidaemic Effect of Fruit Juice of *Emblica officinalis* in Cholesrterol-Fed Rabbits, J. Ethnopharmacology, 50: 61-68 (1996), Elsevier Science Ireland Ltd.

Kim, HJ, Yokozawa, T, Kim, HY, Tohda, C, Rao, TP, and Juneja, LR, Influence of Amla (*Emblica officinalis* Gaertn.) on Hypercholesterolemia and Lipid Peroxidation in Cholesterol-Fed Rats, J. Nutr. Sci. Vitaminol., 51: 413-418 (2005).

Bhattacharya, A, Muruganandam, AV, Kumar, V, and Bhattacharya, SK, Effect of Poly Herbal Formulation, EuMil, on Neurochemical Perturbations Induced by Chronic Stress, Indian J. exp. Biol., 40: 1161-1163 (2002).

Bhattacharya, SK, Bhattacharya, D, and Muruganandam, AV, Effect of *Emblica Officinalis* Tannoids on a Rat Model of Tardive Dyskinesia, Indian J. exp. Biol., 38:945-947 (2000).

One page of International Search Report dated Dec. 1, 2003, from International Appl. No. PCT/IN03/00137.

Seven (7) pages of European Search Report dated Jun. 18, 2009.

Nalini D and Kapoor R, Effect of Plant Fruits: Indian Gall Nut, Bedda Nut and Gooseberry—On Hypercholesterolemic Rats, Plant Foods for Human Nutrition, 53(4):343-349 (1999).

Reza MS, Khan BR, Islam B, Muhsin AUM, and Quddus R, Effects of *Emblica officinalis* (amlaki) and Vitamin C on Cholesterol Induced Atherosclerosis in Rabbits, Journal of Bangladesh College of Physicians and Surgeons 1994 BD, 12(1):3-7 (1994).

Rader, DJ, High-density Lipoproteins and Atherosclerosis, American Journal of Cardiology, 90(8A), 62i-70i (2002).

Protest Documents filed by Third Party on Jul. 3, 2011, thirteen (13) pages.

\* cited by examiner

FIG. 1

Table 7. Effect of the product on Hematological Parameters

| Parameter | Control Group | | | | Intervention Group | | | |
|---|---|---|---|---|---|---|---|---|
| | 0 Month | 1 Month | 2 Month | 3 Month | 0 Month | 1 Month | 2 Month | 3 Month |
| RBC (millions/mm$^2$) | 4.5±0.23 | 4.81±0.37 | 4.88±0.28 | 4.84±0.32 | 4.66±0.28 | 4.72±0.41 | 4.82±0.31 | 4.83±0.23 |
| WBC ('000/mm$^2$) | 6.62±1.39 | 6.03±0.76 | 6.42±0.40 | 6.57±0.40 | 6.7±1.52 | 6.22±1.07 | 6.62±1.04 | 6.77±1.04 |
| Lymphocytes ('000/mm$^2$) | 3.23±0.67 | 3.06±0.52 | 3.06±0.62 | 3.16±0.57 | 2.90±0.59 | 2.89±0.54 | 2.96±0.57 | 3.01±0.68 |
| Hb (g/dl) | 12.09±0.27 | 11.53±0.60 | 11.83±0.37 | 11.92±0.54 | 12.60±1.00 | 12.92±0.50 | 13.04±0.55 | 13.00±0.72 |

FIG. 2

Table 8. Effect of the product on Lipid Profile in Hypercholesterolemic Patients

| Parameter | Control Group | | | | Intervention Group | | | |
|---|---|---|---|---|---|---|---|---|
| | 0 Month | 1 Month | 2 Month | 3 Month | 0 Month | 1 Month | 2 Month | 3 Month |
| Total Chol. | 235.50±51.71 | 234.63±46.52 | 234.38±38.04 | 241±36.18 | 281.90±32.96 | 266.45±28.18 | 251.72±40.93 | 234.45±38.51 |
| VLDL Chol. | 21.63±3.96 | 24.88±5.62 | 29.00±9.77 | 28.13±7.16 | 40.63±14.41 | 40.45±16.13 | 36.00±13.31 | 31.27±15.25 |
| LDL Chol. | 170.75±50.90 | 168.63±45.59 | 163.25±32.35 | 172.00±32.35 | 202.09±19.23 | 193.72±30.59 | 177.27±32.16 | 159.10±43.71 |
| HDL Chol. | 43.13±10.34 | 41.13±6.68 | 42.63±11.13 | 41.25±9.45 | 38.25±7.39 | 41.18±6.76 | 43.45±14.59 | 47.54±10.63 |
| TG | 107.62±19.20 | 117.37±22.49 | 145.87±49.64 | 141.37±35.35 | 208.72±64.76 | 194.45±80.27 | 182.18±56.31 | 159.18±71.78 |

COMPOSITION TO ENHANCE HDL CHOLESTEROL AND TO DECREASE INTIMA-MEDIA THICKENING IN ANIMALS AND HUMANS AND A METHOD FOR ITS PREPARATION

This is a Divisional of U.S. application Ser. No. 13/374,931, filed Jan. 24, 2012, which is a divisional of Ser. No. 12/805,191, filed Jul. 16, 2010, which is a Divisional of U.S. application Ser. No. 11/643,788, filed Dec. 22, 2006, which is a continuation of U.S. application Ser. No. 11/111,798, filed Apr. 22, 2005, which is a continuation of International Application PCT/IN2003/000137, with an international filing date of Apr. 3, 2003 and claiming priority of India Patent Application 169/MAS/2003 filed on Mar. 3, 2003, which documents are all incorporated herein by reference.

TECHNICAL FIELD

This invention relates to a product (nutritional supplement) to correct dyslipidemia, reduce inflammation and to reduce fasting sugar levels in blood in animals and humans and to combat intima-media thickening thus affording significantly improved therapeutic and prophylactic cardioprotection, the said composition being an extract of Emblica officinalis, Gaertn (Euphorbiaceae) prepared without using any organic solvent and without resorting to any chemical processing steps.

BACKGROUND OF THE INVENTION

E. officinalis (Amla) fruit is one of the key constituents of the celebrated Ayurvedic preparation, Chyavanaprash, used in India for thousands of years as a vitalizing and rejuvenating health tonic. The low molecular weight hydrolyzable, gallo- and ellagi tannins (Ghosal, S. et al., Indian J. Chem., 1996, 35B, 941-48) of the fruit provide multi-pronged benefits arising out of their antioxidative, hypocholesterolemic, immunomodulating and HMG CoA reductase inhibitive properties. While its LDL-cholesterol lowering property has been described in published literature, the more desirable property of enhancing HDL cholesterol, as described in the present invention, was not noted before. Similarly, no earlier work had studied the antiinflammatory properties of amla, as observed in the present invention. Reduction of fasting glucose levels consequent to amla consumption is another desirable property observed in the present invention. We have also now surprisingly found that E. officinalis fruit extract reduces intima-media thickening in experimental animals. This observation, though limited to experimental animals, is also reported for the first time. The cumulative effect of the reduction of multiple risk factors by amla extract is the potential regression of this major disease. Thus the beneficial effects of the present inventive composition goes beyond the simple correction of LDL cholesterol levels, as achieved in previous studies.

Coronary heart disease (CHD) continues to be the major cause of premature death in most developed and developing countries. A low level of HDL cholesterol is the second most important risk factor for CHD, as demonstrated in numerous clinical and epidemiological studies (Gorden, D. and Rifkind, H. M., N. Engl. J. Med., 1989, 321:1311-1315; Brewer, Jr., H. B., New Engl. J. Med., 2004, 350:1491-94) and HDL has emerged, during the past decade, as a new potential target for the treatment of cardiovascular diseases. The key role of HDL as a carrier of excess cellular cholesterol in the reverse cholesterol transport pathway is believed to provide protection against atherosclerosis. In reverse cholesterol transport, peripheral tissues, for example, vessel-wall macrophages, remove their excess cholesterol through the ATP-binding cassette transporter 1 (ABCA1) to poorly lipidated apolipoprotein A-I, forming pre-β-HDL. Lecithin-cholesterol acyltransferase then esterifies free cholesterol to cholesteryl esters, converting pre-β-HDL to mature spherical α-HDL.

HDL cholesterol is transported to the liver by two pathways: 1) it is delivered directly to the liver through interaction with the scavenger receptor, class B, type I (SR-BI); 2) cholesteryl esters in HDL are transferred by the cholesterol ester transferase protein (CETP) to very-low-density-lipoproteins (VLDL) and low-density lipoproteins (LDL) and are then returned to the liver through the LDL receptor. HDL cholesterol that is taken up by the liver is then excreted in the form of bile acids and cholesterol, completing the process of reverse cholesterol transport (Brewer, H. B. Jr., Arterioscl. Thromb. Vasc. Biol., 2004, 24:387-91). HDL is believed to have the ability to remove cholesterol from macrophages, thus preventing the formation of foam cells.

A second beneficial role of HDL in atherosclerosis is in protecting LDL from oxidation (Navab, M. et al, Circulation, 2002, 105:290-92). Unlike normal LDL, oxidized LDL is readily taken up by macrophage scavenger receptor SR-A or CD36 resulting in the formation of foam cells. Foam cells are a major component of the early atherosclerotic lesion. Further, HDL may slow the progression of lesions by selectively decreasing the production of endothelial cell-adhesion molecules that facilitate the uptake of cells into the vessel wall (Barter, P. J., et al, Curr. Opin. Lipid, 2002, 13:285-88). HDL may also prolong the half-life of prostacycline and preserve its vasodilatory effect (Mackness, M. I. et al, Atherosclerosis, 1993, 104:129-35).

Several lines of evidence support the concept that increasing the HDL level may provide protection against the development of atherosclerosis. Epidemiologic studies have shown an inverse relation between HDL cholesterol levels and the risk of cardiovascular disease. Increasing the HDL cholesterol level by 1 mg may reduce the risk of cardiovascular disease by 2 to 3 percent. Overexpressing the apo-A-I gene in transgenic mice and rabbits and infusing complexes consisting of apo A-I and phospholipids into hyperlipidemic rabbits increase HDL cholesterol levels and decrease the development of atherosclerosis (Brewer, H B, Jr., loc. cit). In humans, infusing either of these complexes or pro-apo-A-I results in short term increase in HDL cholesterol, biliary cholesterol and fecal cholesterol loss, reinforcing the concept that elevating the HDL cholesterol level decreases the risk of cardiovascular disease.

More than 40 percent of patients with myocardial infarction have low HDL-C as a cardiac risk factor. (Genest, J. J., et al, Am. J. Cardiol., 1991, 67:1185-89). In the prospective and multicentric European Concerted Action on Thrombosis and Disabilities (ECAT) Angina Pectoris Study, Bolibar et al (Thromb. Haemost., 2000, 84:955-61) identified low HDL-C and low apoA-I as the most important biochemical risk factors for coronary events in patients with angiographically assessed CHD. By convention, the risk threshold value of HDL-C has been defined as 35 mg/dL (0.9 mmol/L) in men and 45 mg/dL (1.15 mmol/L) in women [Expert panel on detection, evaluation and treatment of high blood cholesterol in adults. The second report of the National Cholesterol Education Program (NCEP) expert panel on detection, evaluation and treatment of high blood cholesterol in adults (Adult Treatment Panel II). Circulation. 1994; 89:1329-1445)]. Because of interaction, the strength of the association between HDL-C and cardiovascular risk depends on the presence of additional risk factors. Therefore, threshold values are higher in men with diabetes mellitus or hypercholesterolemia or in the presence of multiple risk factors (von Eckardstein A, and Assmann G. *Curr Opin Lipidol*. 2000; 11:627-637). Low HDL-C has been identified as the most frequent familial dyslipoproteinemia in patients with premature myocardial infarction (Genest, J. J. Jr., *Circulation*. 1992; 85:2025-2033). Finally, in the Helsinki Heart Study (Manninen, V. et al, *Circulation*. 1992; 85:37-45) and the High-Density-Lipoprotein Cholesterol Intervention Trial of the Department of Veterans Affairs (VA-HIT) study (Rubins, H. B. et al, *N Engl J Med*. 1999; 341:410-418), increases of HDL-C on treatment with gemfibrozil were correlated with the prevention of CHD events. Thus, HDL-C has become an important component of algorithms to assess the global cardiovascular risk of patients and also a target for therapeutic intervention and for the definition of treatment goals.

Strategies to correct dyslipidemia in atherosclerosis generally involve diet and/or drugs. The threshold serum total cholesterol and LDL cholesterol concentrations above which diet and drug therapy should be initiated, as well as the goals of therapy, have been defined by the National Cholesterol Education Program (*JAMA*, 1993,269:3015-23). The target serum LDL-C is <160 mg/dl (4.3 mmol/l) for patients with no risk factors or only one risk factor for CHD; <130 mg/dl (3.4 mmol/l) for patients with 2 or more risk factors and less than 100 mg/dl (2.6 mmol/l) for those with CHD. Persons with diabetes also fall into the third category. A reasonable target for triglyceride concentration is 200 mg/dl or less; higher values are associated with a doubling of the risk of cardiovascular disease when serum cholesterol concentration exceeds 240 mg/dl or when the LDL-C/HDL-C ratio exceeds 5:1.

A number of studies have shown that reducing serum LDL-C below the target levels does not necessarily result in proportional reduction in the risk of CHD [(The Scandinavian Simvastatin Survival Study Group. Randomized trial of cholesterol lowering in 4444 patients with coronary heart disease, *Lancet*, 1994, 344:1383-89; Shepherd, J. et al, *N Engl. J. Med.*, 1995, 333:1301-7; Sachs, F. M. et al, *N Engl. J. Med.*, 1998, 315:1001-9; *Circulation*, 1998, 97:1446-52; The West of Scotland Coronary Prevention Study Group, *Circulation*, 1998, 97:1440-45; Pederson, T. R., *Circulation*, 1998, 97:1453-60] because of the attenuation of the cholesterol-heart disease relation at lower serum cholesterol concentrations (Grundy, S. M., *Circulation*, 1998, 97:1436-39).

Dietary treatment of hyperlipidemia is a necessary foundation for drug treatment. Depending on the degree of hyperlipidemia, the Step I and Step II diets can be introduced sequentially. The Step II diet contains no more than 30% of calories from fat, less than 7% of calories from saturated fatty acids and less than 200 mg of cholesterol per day. In long term studies, the Step II diet decreased serum LDL-C concentrations 8-15% (Knopp, R. H., et al, *JAMA*, 1997, 278:1509-15; Walden, C. E., *Arterioscl. Thromb. Vasc. Biol.*, 1997, 17:375-82; Denke, M. A., *Arch. Intern. Med.*, 1995, 156:17-26). Diets more restricted in fat than the Step II diet result in little additional reduction in LDL-C, raise serum TG concentration and lower HDL-C.

The point to note, from the above, is that reducing LDL-C alone is of little value in reducing the risk of CHD. Further, diets meant for reducing LDL-C may reduce HDL-C to a similar degree (Hunninghake, D. B. et al, *N. Engl. J. Med.*, 1993, 328:1213-19; Schaefer, E. J., et al, *Arterioscl. Thromb. Vasc. Biol.*, 1995, 15:1079-85); Stefanick, M. L., *N Engl. J. Med.*, 1998, 339:12-20).

Drug therapy is resorted to when the desired effects are not achieved with diets alone. Statins are the most popular among the lipid lowering drugs. These drugs lower serum LDL-C concentrations by upregulating LDL-receptor activity as well as reducing the entry of LDL into the circulation. The maximal reductions achieved with a statin ranges from 24-60%. Statins also reduce the serum TG levels; but they are often insufficient. Statins are ineffective in the treatment of patients with chylomicronemia. Adverse effects of statins include, gastrointestinal upset, muscle aches and hepatitis. Rarer problems include myopathy (muscle pain with serum creatine kinase concentrations more than 1,000 U per liter), rashes, peripheral neuropathy, insomnia, bad or vivid dreams and difficulty in sleeping or concentrating (Abramowica, M., *Med. Lett.*, 1996, 38:67-70; Vgontzas, A. N. et al, *Clin. Pharmacol. Ther.*, 1991, 50:730-37; Roth, T. et al, *Clin. Cardiol.*, 1992, 15:426-32; Partinen, M. et al, *Am. J. Cardiol.*, 1994, 73:876-80). Other lipid-lowering drugs include bile acid-binding resins (e.g., cholesteramine and colestipol), nicotinic acid, and fibrates.

Drug therapy is not recommended for premenopausal women and men under 35 years of age unless they have serum LDL-C concentrations of more than 220 mg/dl (5.7 mmol/l), because their immediate risk of heart disease is low [Summary of the second report of the National Cholesterol Education Program (NCEP): expert panel on detection, evaluation and treatment of high blood cholesterol in adults, *JAMA*, 1993, 269:3015-23].

Thus, diets alone or in conjunction with lipid lowering drugs fail to yield the desired goal of safe lipid lowering. However, this goal is achievable with the present inventive composition containing the active principles of *Emblica officinalis*. Emblica has been in safe use in India for thousands of years as component of Ayurvedic preparations. The composition offers the twin benefits of reducing the harmful LDL cholesterol and enhancing the desirable HDL cholesterol.

Further, the composition was found to reduce the intima-media thickening of the arteries in experimental animals which is an added benefit. Such an effect has not been observed before.

Amla's cholesterol lowering effects have been reported in a few studies. Thakur et al studied the effect of amla on cholesterol-induced atherosclerosis in rabbits (Thakur, C. P. and Mandal, K., Indian J Med Res, 79: 142-6 1984; Thakur C P, et al. Int J Cardiol, 1988, 21:167-75). The control group was fed with cholesterol alone and the experimental group, amla and cholesterol for 16 weeks. Cholesterolemia was found to be significantly less in amla group (205 mg/dl) than in the control group (630 mg/dl). Aortic sudanophilia was significantly less in the amla group (12%) than in the control group (38%). The cholesterol contents of the liver and aorta, respectively, were significantly less in the amla group (46 mg/100 g, 42 mg/100 g), than in the control group (604 mg/100 g, 116 mg/100 g). Amla did not influence serum triglyceride (TG) levels, euglobulin clot lysis time or platelet adhesiveness. Another study (Mather R, et al. J Ethnopharmacol, 1996, 50:61-68) found that serum cholesterol, TG, phospholipids and LDL cholesterol were lowered 82%, 66%, 77% and 90%, respectively, when fresh amla juice was fed to rabbits. Aortic plaques were regressed. Amla juice-treated rabbits excreted more cholesterol and phospholipids. Similar results have been reported by others (Mishra M, et al. Br J Exp Pathol, 1981, 62:526-28; Tariq M, et al. Indian J Exp Biol, 1977, 15:485-86).

Amla was found to inhibit cholesterol synthesis in rats (Anila I, Vijayalakshmi N R, J Ethnopharmacol, 2002, 79:81-87) by inhibiting the cholesterol synthesizing enzyme HMG CoA reductase. Degradation and elimination of cholesterol was noted, and thus the hypercholesterolemia induced by amla was suggested to be due to inhibition of synthesis and enhancement of degradation.

Oxidized LDL (ox-LDL) is one of the etiological factors of atherogenesis. A study was conducted to see if the antiatherogenic effects of amla was due to its effect on ox-LDL (Duan W, et al. Yakagaku, 2005, 125:587-91). Human umbilical vein endothelial cells (HUVEC) was incubated with ox-LDL and corilagin and its analogue Dgg 16 (present in amla) and then incubated with monocytes. Malondialdehyde (MDA) in the culture media was then determined. Monocytes adhering to the HUVEC were counted by cytometry. In another experiment, rat vascular smooth muscle cells (VSMC) were incubated in the media with or without ox-LDL and with corilagin and Dgg 16 at different doses and cell proliferation was assayed. Both corilagin and Dgg 16 were able to reduce MDA, prevented HUVEC from adhering to monocytes, and inhibited VSMC proliferation induced by ox-LDL. The authors concluded that the antiatherogenic effect of amla is due to corilagin and Dgg-16. Ethyl acetate extract of amla was a stronger antioxidant than probucol in preventing LDL oxidation (Kim H J, et al. J Nutr Sci Vitaminol, 2005, 51:1812-18).

So far no study has reported the HDL enhancing effect of amla, as described in the present invention.

Inflammation

An important component of atherosclerotic process is inflammation (Ross, R, N Engl J Med, 1999, 340:115-26; Libby P, Nature, 2002, 420:868-74). The fundamental appreciation that inflammation is an important and possibly even obligatory component of lesion initiation and progression, and also participates in the plaque rupture that mediates thrombotic complications and clinical events, has fundamentally changed the view of the pathogenesis of atherosclerosis. Thus correcting dyslipidemia alone does not reduce the risk of cardiovascular disease, or of clinical events in patients with established disease.

Considering the importance of inflammation in atherosclerosis, attention has been directed to search for mediators which are appropriate for monitoring inflammation. The most reliable marker for inflammation has been found to be the blood levels of C-reactive protein (CRP) (Pepys M B, Hirschfield, G M, J Clin Invest, 2003, 111:1805-12; Ridker P M, et al. N Engl J Med, 2005, 352:20-28). Clinical studies have shown the association of elevated plasma levels of CRP and increased cardiovascular risk (Shishehbor M H, et al. Cleve Clin J Med, 2003, 70:634-40). Especially chronically elevated CRP levels measured by high sensitive assays (hs-CRP) can independently predict the risk of cardiovascular events (Ridker P M, Circulation, 2003, 107:363-69). Patients with acute coronary syndrome often have elevated plasma levels of CRP (Nieminem M S, et al. Eur Heart J, 1993, 14:(suppl K):12-16). CRP has also been reported to determine the prognosis of developing arterial ischemia in healthy persons (Ridker P M, et al, N Engl J Med, 2000, 342:836-42; Harris T B, et al. Am J Med, 1999, 106:506-12; Ridker P m et al, JAMA, 2001, 285:2481-85). In patients with cardiovascular disease who underwent coronary intervention, it can predict the risk of developing myocardial infarction and death (Chew D P et al, Circulation, 2001, 104:992-97; Lenderink T, et al. Eur Heart J, 2003, 24:77-86). CRP is a sensitive marker for inflammation leading to arteriosclerosis and monitors the inflammatory process in the arterial wall. It also has a direct influence on arterial injury. In the presence of CRP, endothelial adhesion molecules are significantly upregulated (Paceri V, et al. Circulation, 2000, 102:2165-68). CRP furthermore can stimulate monocytes to produce tissue factor, an important initiator of the clotting cascade (Cermal J, et al. Blood, 1993, 82:513-20). These data underlie the utility of CRP measurements in predisposed persons, and also suggest role for antiinflammatory therapy in those patients. It has been suggested that patients with coronary artery disease do benefit from reduction of CRP levels (Tomoda H, Akoi N, Am Heart J, 2000, 140:324-28; Ridker P M et al. Circulation, 1999, 100:230-35; Ridker P M, et al. N Engl J Med, 2005, 352:20-28).

CRP, thus, is not just a marker of inflammation, but an agent involved in the atherogenic process as well as a predictor of future cardiac events. Hence the need to keep the CRP to normal levels.

Amla's effect on CRP and on inflammation in general, has not been reported earlier. In one embodiment, the disclosed amla product has been found to be a robust agent to reduce CRP in human volunteers in the present invention.

Hyperglycemia

Diabetes mellitus magnifies the risk of cardiovascular morbidity and mortality (Resnick He, et al. J Clin Epidemiol, 2001, 54:869-76; Beckman J A, et al. JAMA, 2002, 287:2570-81). Besides the well-recognized microvascular complications of diabetes such as nephropathy and retinopathy, there is a growing epidemic of macrovascular complications including diseases of the coronary arteries, peripheral arteries and carotid vessels, particularly in the burgeoning type 2 diabetic population.

Coronary artery disease (CAD) causes much of the serious morbidity and mortality in diabetic patients who have a 2- to 4-fold increase in risk of CAD (Haffner S M, et al. N Engl J Med, 1998, 339:229-234). This has been observed a number of large trials (Kjaergaard Sc, et al, Scand J Cardiovasc J, 1999, 33:166-70; Malmberg K, et al, Circulation, 2002, 102:1014-19; Zuanetti G, et al. J Am Coll Cardiol, 1993, 22:1788-94; Shindler D M et al, J Am Coll Cardiol, 2000, 36:1097-1103). Patients with diabetes also have an adverse long-term prognosis after myocardial infarction (MI), including increased rates of reinfarction, congestive heart failure and death (Malmberg K, et al, Circulation, 2002, 102:1014-19). A Finnish study on trends of MI showed that diabetes increased 28-day mortality by 58% in men and 160% in women (Miettinen H, et al., Diabetes Care, 1998, 21:69-75). The 5-year mortality rate following MI may be as high as 50% for diabetic patients, more than double that of nondiabetic patients (Herlitz J, et al. Diabetes Med, 1998, 15:308-14). Such results led the Adult Treatment Panel III of the National Cholesterol Education Program to establish diabetes as a CAD risk equivalent mandating aggressive antiatherosclerotic therapy (JAMA, 2001, 285:2486-97).

Hyperglycemia (increased blood sugar levels), a cardinal manifestation of diabetes, adversely affects vascular functions, lipids, and coagulation. Intensive treatment of hyperglycemia reduces the risk of microvascular complications such as nephropathy and retinopathy, as shown by the United Kingdom Prospective Diabetes Study (UKPDS) (UKPDS 33, Lancet, 1998, 352:837-53). In a meta-analysis of more than 95,000 diabetic patients, increases in cardiovascular risk depended directly on plasma glucose concentrations and began with concentrations below the diabetic threshold (Coutinho M, et al. Diabetes Care, 1999, 22:233-40).

Diabetes also causes abnormalities in lipid profile, including elevated triglyceride levels, decreased HDL levels and increased levels of small, dense LDL. Elevated levels of triglyceride-rich lipoproteins lower HDL levels by promoting exchanges of cholesterol from HDL to VLDL (Sniderman A D, et al. Ann Intern Med, 2001, 135:447-59). Diabetic patients with CAD more commonly have elevated triglyceride and low HDL levels than elevated total cholesterol and LDL cholesterol levels (Rubins H B, et al. Am J Cardiol, 1995, 75:1196-1201). HDL normally protects LDL from oxidation, but this ability is impaired in diabetic patients (Gowri M S, et al. Arterioscl Thromb Vasc Biol, 1999, 19:2226-33).

Thus controlling hyperglycemia is important to prevent diabetic as well as cardiovascular complications.

Hypoglycemic effects of amla has not been described earlier. However, such effects of two polyherbal compositions (Triphala and Hyponidd) of which amla is a constituent have been reported (Sabu M C, Kuttan R, J Ethnopharmacol, 2002, 81:155-60; Babu P S et al. J Pharm Pharmacol, 2004, 56:1435-42). Triphala is a mixture of three herbal extracts, whereas ten herbs constitute Hyponidd. The latter also contain known hypoglycemic herbs such as Momordica charantia and Gymnema sylvestre. As described in the present invention, the amla product is found to possess hypoglycemic properties.

Thyroid Dysfunction

Thyroid hormone excess and deficiency are common (Hollowell J G, et al. J Clin Endocrinol Metab, 2002, 87:489-99; Vanderpump M P, et al. Clin Endocrinol (Oxford), 1995, 43:55-68) and are readily diagnosed and treated. A number of studies suggest that abnormal levels of thyroid stimulating hormone (TSH) may represent a novel risk factor for cardiovascular diseases (Hak A E, et al. Ann Intern Med, 2000, 132:270-78; Parle T V, et al. Lancet, 2001, 358:861-65; Imaizumi, M, et al. J Clin Endocrinol Metab, 2004, 89:3365-70; Kvetny J, et al. Clin Endocrinol (Oxford), 2004, 61:232-38; Walsh J P, et al. Arch Intern Med, 2005, 165:2467-72). Even mildly altered thyroid status reportedly affects serum cholesterol levels (Danese M D, et al. J Clin Endocrinol Metab, 2000, 85:2993-3001; Vierhapper H, et al Thyroid, 200, 10:981-84; Canaris G J, et al. Arch Intern Med, 2000, 150: 526-34) heart rhythm (Sawin C T, et al. N Engl J Med, 1994, 331:1249-52) and rate (Bell G M, et al. Clin Endocrinol (Oxford), 1983, 18:511-16), ventricular function (Biondi B, et al. J Clin Endocrinol Metab, 2000, 85:4701-05; Idem, Ibid, 1999, 84:2064-67), risk of coronary artery disease (Hak A E, Loc cit; Walsh J P, loc cit; Cappola A R, et al. J Clin Endocrinol Metab, 2003, 88:2438-44).

Thyroidisms are classified into various categories (Cappola A R, et al. JAMA, 2006, 295:1033-41) as euthyroidism (normal TSH concentrations (0.45 to 4.5 mU/L), subclinical hyperthyroidism (TSH concentration 0.10 to 0.44 mU/L0, or less than 0.10 mU/L with a normal free thyroxine (FT4) concentration; subclinical hypothyroidism (TSH concentration more than 4.5 mU/L and less than 20 mU/L with a normal FT4 concentration, and overt hypothyroidism with a TSH concentration of 20 mU/L or more. In overt hyperthyroidism, the TSH levels are suppressed much below the normal levels, usually undetectable, or can be measured in a third-generation assay capable of detecting 0.01 mU/L (Shrier M D, Burman K D, Am. Fam Phys, 2002, 65:431-38).

Thyroid hormone has relevant effects on the cardiovascular system (Klein I, Ojama K, N Engl J Med, 2001, 344:501-09; Fazio, S et al. Recent Prog Horm Res, 2004, 59:31-50). Many symptoms and signs recognized in patients with overt hyper- and hypothyroidisms are due to the increased or reduced action of the thyroid hormone on the heart and vascular system, respectively Subclinical thyroid dysfunction may affect the cardiovascular system, which may increase the cardiovascular risk. In addition, patients with acute or cardiovascular disorders have abnormalities in peripheral thyroid hormone metabolism that may alter cardiac functions. The morbidity and mortality associated with hypothyroidism are apparently related to the atherogenic and prothrombotic vascular modifications that follow thyroid hormone deficiency, whereas heart failure and particularly atrial fibrillation and its thromboembolic complications are the primary consequences of hyperthyroidism. In both cases, return to normal thyroid levels corrects the cardiac abnormalities caused by thyroid dysfunction.

Amla has been found to be beneficial in hyperthyroidism, though the study was limited to mice (Panda S, Kar A, Pharmazie, 2003, 58:753-56). Amla fruit extract was evaluated for its effects on the L-thyroxine (L-T4)-induced hyperthyroidism in mice. While an increase in serum T3 (triiodothyronine) and T4 (thyroxine) concentrations, and in a thyroid dependent parameter, hepatic glucose 6-phospatase (glu-6-pase) activity was observed in L-T4 (0.5 mg/kg/d) treated animals, simultaneous oral administration of the plant extract at a dose of 250 mg/kg/d (p.o.) for 30 days in hyperthyroid mice reduced T3 and T4 concentrations by 64 and 70% respectively as compared to a standard antithyroid drug, propyl thiouracil that decreased the levels of the thyroid hormones by 59 and 40% respectively. The plant extract also maintained nearly normal value of glu-6-pase activity in hyperthyroid mice.

Results reported in the present invention is the first report on the effect of amla in thyroid dysfunction in humans.

Intima-Media Thickening

The increased thickness of intima plus media of the carotid artery is associated with the prevalence of cardiovascular diseases and a number of studies have shown a positive association between cardiovascular risk factors and carotid intima-media thickness (IMT)(O'Leary, D. H. et al., Stroke, 1992, 22:1156-63; 1992, 23:1752-60; New Engl. J. Med., 1999, 340(1):14-22; Howard, N. et al, Ann. Int. Med., 1998, 128(4):262-69); Zureik, M. et al, Stroke, 1999, 30:550-55; del Sol, A. I. et al, Stroke, 2001, 32:1532-38). Howard et al (loc.cit.) makes the following statement: For each 0.03 mm increase per year in carotid arterial IMT, the relative risk for non-fatal myocardial infarction or coronary death was 2.2 (95% CI, 1.4-3.6) and the relative risk for any coronary event was 3.1. Absolute IMT was also related to risk for clinical coronary events. Absolute thickness and progression in thickness predicted risk for coronary events beyond that predicted by coronary arterial measures of atherosclerosis and lipid measurements. A growing number of epidemiological studies and clinical trials use IMT as an early marker of systemic atherosclerosis (Zanchetti, A., et al, J. Hypertens., 1998, 16:949-61; MacMahon, S. et al, Circulation, 1998, 97:178-90: Borhani, N. O. et al, JAMA, 1996, 124:548-56; Hodis, H. N. et al, Ann. Intern. Med., 1996, 124:548-52).

IMT is increasingly being used in clinical trials as surrogate end point for determining the success of interventions that lower risk factors for atherosclerosis. To distinguish early atherosclerotic plaque formation from thickening of the intima-media, the following consensus has evolved (Touboul, P. J. et al, Mannheim Intima-Media Thickness Consensus. on Behalf of the Advisory Board of the 3rd Watching the Risk Symposium 2004, 13th European Stroke Conference, Mannheim, Germany, May 14, 2004, Cerebrovasc. Dis., 2004, 18(4):346-49): Plaque is defined as a focal structure that encroaches into the arterial lumen of at least 0.5 mm or 50% of the surrounding IMT value or demonstrates a thickness of ≥1.5 mm as measured from the media-adventitia interface to the intima-lumen interface. Standard use of IMT measurements is recommended in all epidemiological and interventional trials dealing with vascular diseases to improve characterization of the population investigated.

Endothelial vasodilator dysfunction and carotid IMT are two indicators of subclinical cardiovascular disease. In a study of a large, community-based cohort of young adults (aged 24-39 years), Jounala et al (*Circulation,* 2004, 110(18): 2918-23) found that IMT was inversely associated with endothelium-dependent brachial artery flow-mediated dilation (FMD). The number of risk factors was correlated with increased IMT in subjects with evidence of endothelial dysfunction. In a related study, FMD and glyceryl trinitrate-induced endothelium-independent vasodilation (GTN) were measured in the brachial artery. IMT of the common carotid artery and insulin sensitivity were also measured. There was a significant positive relation between insulin resistance, as measured by steady-state glucose levels, and IMT. Insulin resistance was negatively correlated with both FMD and GTN. This indicates that both FMD and GTN were also negatively correlated with IMT (Suzuki, M. et al., *Am. J. Hypertens,* 2004, 17(3):228-32). Similarly, in a study on 252 healthy adults, IMT was significantly greater in subjects with subclinical aortic valve sclerosis (Yamamura, Y., et al, *Am. J. Cardiol.,* 2004, 94(6):837-39). To determine whether IMT is related to an increased risk of cardiovascular event after percutaneous coronary angioplasty (PTCA), IMT was measured within 2 days following PTCA in 88 patients (mean age 62 years) in another study. A common carotid IMT >0.7 mm was associated with an increased risk of cardiac events after PTCA (Lacroix, P. et al., *Int. Angiol.,* 2003, 22(3):279-83).

Low HDL cholesterol was associated with increased IMT independent of other risk factors in healthy subjects from families with low HDL cholesterol (Alagona, C., et al, *Eur. J. Clin. Invest.,* 2003, 33(6):457-63). Conversely, increased HDL cholesterol was negatively correlated with IMT (Blankenhorn, D. H., et al, *Circulation,* 1993, 88(1)20-28; Bonithon-Kopp, C. et al, *Arterioscl. Thromb. Vasc. Biol,* 1996, 16:310-16).

A statistically significant IMT greater than 0.8 mm was associated with coronary artery disease with an odds ratio of 2.4 in Indian subjects (Jadhav, U. M. and Kadam, N. N., *Indian Heart. J.,* 2001, 53(4):458-62). The same authors also found (*J. Assoc. Physicians India,* 2002, 50:1124-29) a statistically significant association of microalbuminuria with IMT and coronary artery disease in diabetic patients.

In a large population-based of 6943 subjects, carotid IMT and aortic calcification were found to be the strongest predictors of stroke (Hollander, M. et al., *Stroke,* 2003, (10):2368-72).

From the foregoing, the importance of IMT in cardiovascular disease management is amply evident. Fortunately, IMT is modifiable. Various synthetic drugs, for example, colestipol plus niacin (Blankenhorn, D. H., *Circulation,* 1993, 88(1):20-28), candesartan (Igarashi, M. et al, *Hypertension,* 2001, 38(6):1255-59), simvastatin (Detmers, P. A., et al, *Circulation,* 2002, 106(1):20-23), rampamycin with tacrolimus or cyclosporin (Weller, J. R., et al, *Br. J. Surg.,* 2002, 89(11): 1390-95), calcium channel blockers (Wang, J. G. and Staessen, J. A., *J. Am. Soc. Nephrol.,* 2002, 13 Suppl:S208-15), sulfated oligosaccharide PI-88 (Francis, D. J., et al, *Circ. Res.,* 2003, 92(18):70-77), fluvastatin (Ye, P. et al, *Chin. Med. Sci. J.,* 2000, 15(3):140-44), lovastatin (Furberg, C. D., et al, *Circulation,* 1994, 90:1679-87), chemically modified tetracycline (Islam, M. M., et al, *Am. J. Pathol.,* 2003, 163(4): 1557-66) reduce IMT. There are very few natural products which are reported to suppress intimal thickening. Thus, the finding that Emblica extract can reduce IMT assumes great significance.

The disclosed amla product was found to reduce IMT in rabbits. Though the reduction in IMT has not been proven in humans, it is expected such results may be achieved in human beings as well because IMT is inversely associated with HDL concentration (Watanabe et al. Arterioscl Thromb vasc Biol, 2006, 26:897-902; Alagona C et al. Atherosclerosis, 2002, 165:309-16; Eur J Clin Nutr, 2003, 33:457-63). IMT is also positively correlated with CRP (Wang T S et al. Arterioscl Thromb Vasc Biol, 2002, 22:1662-67; Sitzer M, et al. J Cardiovasc Risk, 2002, 9:97-103). Diabetes is also associated with increased IMT (Mohan V, et al. Diabetes Med, 2006, 23:845-50; Wagenknecht L E et al. Diabetes Care, 1998, 21: 1812-18; Brohall G, et al. Diabet Med, 2006, 23:609-16). Thus, it is reasonable to expect that the disclosed amla product would reduce IMT, indirectly indicating regression of atherosclerosis.

The present inventive composition, by its direct effects on dyslipidemia, inflammation, hyperglycemia and intima-media thickening, thus offers much improved cardioprotection than any other similar product, natural or synthetic, with the added benefit of its time-tested safety.

Ghosal has disclosed a process for preparation of an extract of *Emblica officinalis* (U.S. Pat. No. 6,124,268) and a few more by the same inventor for various applications of the preparation, such as, stabilization of vitamin C (U.S. Pat. No. 6,235,721), inhibiting platelet aggregation (U.S. Pat. No. 6,290,996) and antioxidant to block free radical process (U.S. Pat. No. 6,362,167). In none of the above patents, the hypocholesterolemic action, and more specifically, its HDL enhancing property or other properties described in the present invention, have been described. The present inventive preparation also materially differs in composition from that described by Ghosal. The extraction process described by Ghosal involves treating the fruit pulp with water containing 1% sodium chloride which was then left at room temperature for 12 hours followed by keeping the mixture at 10° C. for 3 days and thus is very time-consuming, costly and tedious. Further, he uses sodium chloride solution for extraction and apparently, the salt remains in the final preparation. This may not be desirable, given the adverse affects of salts for patients with hypertension which is closely associated with cardiac diseases. Further, going by the examples given in the said Ghosal patent, the content of active principles, which he calls as the antioxidant fraction, is less than 4% in the final preparation. Thus, a more commercially attractive process would be highly desirable.

BRIEF DESCRIPTION OF THE INVENTION

Accordingly, the present invention provides for a preparation an extract of amla, with standardized contents of bioactive principles suitable for therapeutic as well as prophylactic treatment of dyslipidemia, reduction of inflammation and cardiovascular events by lowering CRP levels, reduction of fasting blood sugar levels thus lowering diabetic and cardiovascular complications induced by hyperglycemia and correct thyroid dysfunction. The disclosed Amla product thus affords complete protection against the major risk factors of cardiovascular diseases. This is further demonstrated by the reduction in intima-media thickness of arteries indicating the power of the disclosed amla product in reversing the atherosclerotic process. Reduction of the harmful LDL cholesterol, and more importantly, the enhancement of the beneficial HDL cholesterol was observed. Though this has not been proven in humans, it is expected such results may be achieved in human beings as well because IMT is inversely associated with HDL concentration and any intervention to increase serum HDL-C level would reduce IMT.

One objective of the present invention is to provide a safe natural product for treatment of lipid disorders connected with coronary heart disease and stroke without the disadvantages associated with the use of synthetic lipid lowering agents such as statins. More specifically, the invention aims at providing a composition which lowers the harmful total cholesterol, LDL cholesterol and triglycerides, and at the same time increasing the beneficial HDL cholesterol contents. Low HDL cholesterol is considered as the second most important predictor of coronary heart disease (CHD).

Another objective of the present invention is to provide for a safe, natural product composition to reduce plasma CRP levels and inflammation associated with atherosclerosis, thus reducing risk for future clinical events such as myocardial infarction and stroke.

Another objective of the present invention is to provide for a safe, natural product composition to reduce hyperglycemia in diabetic and pre-diabetic patients, who are at increased risk of coronary artery diseases as well as reduce the risk of microvascular complications associated with diabetes such as nephropathy and retinopathy.

Another objective of the present invention is to provide for a safe, natural product composition to potentially reduce the intima-media thickness of the arteries. Another objective of the invention is to provide for a composition for potential reduction of intima-media thickening observed in heart patients and which is considered as an important marker and predictor of CHD.

Another objective of the present invention is to provide a safe, natural product composition to correct thyroid dysfunction, which is now recognized as a risk factor for cardiovascular diseases.

The present invention thus aims at providing a safe natural product composition to reduce the risk factors associated with coronary artery diseases and induce remission.

A further objective of the present invention is to provide an easy and economical process for the commercial preparation of *E. officinalis* extract offering the benefits described above.

A further objective of the invention is to provide a method of producing a product to correct hypercholesterolemia in a human including:

pulping fruits of *Emblica Officinalis* with demineralized water to create a slurry;

treating the slurry with pectinase to form a pectinase-treated slurry;

filtering the pectinase-treated slurry to create a solution; and concentrating the solution to generate the product.

These and further objectives of the invention will be apparent from the detailed description of the invention given below.

BRIEF DESCRIPTION OF THE FIGURES

FIG. 1 shows Table 7, which provides the effect of product on hematological parameters in human patients; and FIG. 2 shows Table 8, which provides effect of product on lipid profile in hypercholesterolemic patients.

DETAILED DESCRIPTION OF THE INVENTION

The three important components of coronary artery diseases are lipids, inflammation and immunity (for example, see Binder C J, et al. Nature Med, 2002, 8:1218-26). What initiates the atherosclerotic process is not entirely clear, and there are probably several different pathogenic processes that can elicit localized inflammatory responses in the artery. One prime candidate is minimally oxidized LDL, and late forms of oxidized LDL (ox-LDL). Once trapped in the artery wall by binding to extracellular proteoglycans, a key event in atherogenesis (Williams K J and Tobas I, Curr Opin Lipidol, 1998, 9:471-74; Skalen K, et al. Nature, 2002, 417:750-54), LDL is oxidized by mechanisms still unknown or undergoes other types of modifications, such as non-enzymatic glycation, enzymatic degradation, aggregation, or a combination of these, all of which results in alteration of the 'self'. These modifications makes the modified LDL and leads to both cellular and humoral responses (Horkko, S, et al. Free Radic Biol Med, 2000, 28:1771-79. In addition, the oxidation of LDL generates oxidized lipids that are toxic, proinflammatory and pro-atherogenic (Pratico D, Trends Cardiovasc Med, 2001, 11:112-16). Oxidized phospholipids can induce artery wall cells to secrete chemotactic molecules (chemokines), activate endothelial cells to express adhesion molecules, and induce expression of growth factors that facilitate the transformation of monocytes to macrophages and stimulate the proliferation of smooth muscle cells (Berliner J A, et al. Trends Cardiovasc Med, 2001, 11:112-16; Marathe G K, et al. Trends Cardiovasc Med, 2001, 11:139-42). Macrophages, a central mediator in innate and adaptive immunity, are essential in lesion initiation and progression (Glass C K and Witztum J L, Cell, 2001, 104:503-16; Hansson G K, et al. Circ Res, 2002, 91:281-91). Once activated they initiate oxidation of LDL and rapidly take up oxLDL through specific scavenger receptors leading to foam cell formation (Witztum J l, et al. trends Cardiovasc Med, 2001, 11:93-102). This is a key event in disease progression. Activated macrophages also secrete a variety of pro-inflammatory molecules that affect lesion progression and plaque stability.

The present invention provides for a natural product that has been found to directly influence two of the three components, namely lipid disorder and inflammation, of coronary artery diseases discussed above, with potential for modulating the third component, namely immunity, as well. It would be difficult to assess the involvement of amla in modulating the immune system component, but earlier studies have clearly shown its immunomodulating properties (Nemmani K V et al. Indian J Exp Biol, 2002, 40:282-87; Muruganandam A V, et al. Indian J Exp Biol, 2002, 40:1150-60; Bhattacharya A, et al. Indian J Exp Biol, 2002, 40:1161-63; Sai Ram. M, et al. J Ethnopharmacol, 2002, 81:5-10; Phytother Res, 2003, 17:430-33; Bhattacharya S K et al. Indian J Exp Biol, 2000, 38:945-47).

Thus, one embodiment of the disclosed amla product modulates all the important components of coronary artery diseases to induce regression of the disease. Further, one embodiment of the disclosed amla product reduces the fasting blood sugar levels, a confounding factor in atherosclerosis. The potential of the disclosed amla product in inducing regression is shown by the reduction in intima-media thickness in experimental animals.

The present invention provides for a safe natural product for treatment of disorders connected with coronary artery diseases, such as coronary heart disease, stroke and peripheral artery disease, without the disadvantages associated with the use of synthetic lipid lowering agents such as statins.

More specifically, the invention aims at providing a composition which lowers the harmful LDL cholesterol and triglycerides and at the same time increasing the beneficial HDL cholesterol contents. Low HDL cholesterol is considered as the second most important predictor of coronary heart disease (CHD) risk. One embodiment of the disclosed amla product thus corrects dyslipidemia associated with coronary artery diseases.

One embodiment of the disclosed amla product further reduces inflammation which is an integral part of coronary artery diseases, as evidenced by reduction in CRP levels. Since CRP is a predictor of future coronary events, reduction in CRP by the disclosed amla product indicates that the amla product directly affords reduction in risks of clinical events such as myocardial infarction and stroke.

Furthermore, one embodiment of the disclosed amla product reduces the blood sugar levels in diabetics who are at an elevated risk of heart diseases and corrects dyslipidemia associated with diabetes.

One embodiment of the amla product was also found to correct thyroid dysfunction (both hypo- and hyperthyroidisms) which has a direct effect on heart and vascular systems, and now recognized as a risk factor for cardiovascular diseases.

Further, though limited to animal studies, the composition was found to prevent smooth muscle cell proliferation and to reduce the intima-media thickening associated with the process.

The present invention provides for a safe natural product for treatment of lipid disorders connected with coronary heart disease and stroke without the disadvantages associated with the use of synthetic lipid lowering agents such as statins. More specifically, the invention aims at providing a composition which lowers the harmful LDL cholesterol and triglycerides and at the same time increasing the beneficial HDL cholesterol contents. Low HDL cholesterol is considered as the second most important predictor of coronary heart disease (CHD) risk. Further, though limited to animal studies, the composition was found to prevent smooth muscle cell proliferation and to reduce the intima-media thickening associated with the process.

The present composition uses the extract of fresh fruits of *Emblica officinalis*, a tree that occupies a prime position in Ayurvedic preparations for its rejuvenating, vitalizing properties and above all its time-tested safety record. Amla is known as an immunomodulator and this property also is believed to be acting in concert with the observed effects to further induce remission of the disease. The extract is processed as detailed below to contain a minimum amount of active constituents which are believed to be the low molecular weight hydrolyzable tannins, especially, emblicanin A.

In one embodiment of the process, the invention provides for a composition to correct lipid disorders associated with coronary heart disease, namely high LDL cholesterol and triglycerides and low HDL cholesterol in blood.

In another embodiment, the invention provides for a composition to reduce inflammation associated with coronary artery diseases, as evidenced by the reduction in blood CRP levels.

In a further embodiment, the invention provides for a composition to reduce blood sugar levels which has a confounding effect on heart diseases.

In another embodiment, the invention provides for a composition to correct thyroid dysfunctions.

In another embodiment of the invention a composition is provided for reducing the major risk factors associated with coronary artery diseases and induce remission of the disease as evidenced by reduction in the intima-media thickness which is increasingly being used as a marker for heart diseases. Very few natural products have been reported to possess this capability.

In yet another embodiment, the invention provides for a process for the commercial scale preparation of such a composition without the use of any organic solvent and without any chemical treatment or additives and thus possesses much superior properties than any of the lipid lowering agents known.

Accordingly, the pulp obtained from fresh amla fruits was treated with a pectinase enzyme for a sufficient length of time at room temperature. The slurry was filtered to yield a clear filtrate which was then spray-dried to get the composition as a dry, free-flowing powder.

The product was then encapsulated in hard gelatin capsules to contain 500 mg of the spray-dried powder which supplies a minimum of 10 wt % of emblicanin A.

In one embodiment, the invention provides a product having an extract of fruits of *Emblica Officinalis*, wherein the extract is prepared without using any organic solvent and without subjecting to any chemical treatment at any stage.

In one embodiment, the invention provides a method of producing a product including:

pulping fruits of *Emblica Officinalis* with demineralized water to create a slurry;

treating the slurry with pectinase to form a pectinase-treated slurry;

filtering the pectinase-treated slurry to create a solution; and concentrating the solution to generate the product.

In one embodiment, the invention provides a method of producing a product to correct hypercholesterolemia in a human.

Acute and sub-acute toxicities of the products were tested in mice and rats, respectively. Up to a dosage level of 10 g/kg body weight produced no adverse effects such as increased motor activity, tremors, clonic convulsions, piloerection, muscle spasm, hyperesthesia, ataxia, sedation, hypnosis and analgesia in mice. No mortality was recorded in 72 hours. Sub-acute toxicity studies at a dosage level of 2 g/kg body weight for 3 months produced no toxic effects in rats.

The hypocholesterolemic properties of the composition were tested in rabbits. Rabbits were made hypercholesterolemic by oral feeding of cholesterol for 4 months. At the end of 4 months, the treatment groups were administered with the inventive composition for an additional 4 months. Body weight measurements, haematological parameters and lipid profiles of the animals were determined at regular intervals. A near-reversal of the hypercholesterolemic conditions were observed in these animals. There was also reduced activity of the cholesterol-synthesizing enzyme HMG CoA reductase and surprisingly, the thickness of intima plus media also were reduced to normal levels.

The lipid lowering properties of the composition were further tested in hypercholesterolemic human volunteers. The results were in general agreement with those observed in the animal studies. More importantly, there was significant increase in the beneficial HDL cholesterol levels. Recent research has indicated that increasing the HDL cholesterol level is even more important than reducing the LDL cholesterol level.

The composition was further tested in apparently healthy human volunteers, for its effect on blood CRP levels and fasting blood sugar levels, in addition to its effect on the lipid profiles. The composition showed positive benefits in these aspects as well. Blood CRP level is a marker for systemic inflammation and a predictor of future cardiac events. Blood sugar has a confounding effect on the disease.

The product can be administered to a human for a method of reducing serum cholesterol levels. The product can be administered to a human for a method of reducing at least one of serum LDL and VLDL cholesterol concentrations. The product can be administered to a human for a method of enhancing HDL cholesterol levels. The product can be administered to a human for a method of reducing triglyceride to correct dyslipedemia. The product can be administered to a human for a method of preventing smooth muscle cell proliferation and reducing intima media thickening. The product can be administered to a human for a method of reducing HMG CoA reductase activity.

The product can be administered to a human for a method of correcting dyslipedemia. The product can be administered to a human for a method of reducing inflammation. The product can be administered to a human for a method to reduce fasting sugar levels in the blood. The product can be administered to a human for a method of therapeutic and prophylactic cardioprotection. The product can be administered to an atherosclerotic human patient for a method to induce regression of the atherosclerotic process, whereby dyslipedemia, inflammation and blood sugar levels are also corrected. The product can be administered to a human patient having coronary artery diseases to induce regression of atherosclerotic process. The product can be administered to a patient having coronary artery diseases to correct lipid abnormalities. The product can be administered to a patient having coronary artery diseases to reduce serum total cholesterol. The product can be administered to a patient having coronary artery diseases to reduce VLDL cholesterol. The product can be administered to a patient having coronary artery diseases to reduce LDL cholesterol. The product can be administered to a patient having coronary artery diseases to reduce triglyceride concentration. The product can be administered to a patient having coronary artery diseases to elevate beneficial HDL cholesterol. The product can be administered to a patient having coronary artery diseases to reduce inflammation associated with coronary artery disease. The product can be administered to a patient having coronary artery disease to reduce C-reactive protein. The product can be administered to a human to correct hypothyroidism. The product can be administered to a human to correct hyperthyroidism.

In one embodiment, the invention provides for a method of producing a product to correct hypercholesterolemia in a human by pulping fruits of *Emblica Officinalis* with demineralized water to create a slurry. The slurry is treated with pectinase to form a pectinase-treated slurry. The pectinase-treated slurry is filtered to create a solution. The solution is concentrated to generate the product.

These and other features of the present invention are explained in more detail in the following non-limiting examples.

Example 1

Five hundred kilograms of fresh amla fruits were pulped with an equal quantity of demineralized water and the slurry was treated with 2 wt % of pectinase enzyme under stirring at room temperature for 6 h and then filtered to yield 310 liters of the extract with a solids content of 4.8%. This solution was then concentrated below 60° C. to obtain a slurry with a solids content of 15.2%. This was then spray-dried (inlet temperature 180° C., outlet temperature 90° C.) to obtain 13.5 kg of a free flowing powder. The hydrolysable tannin content of this preparation was at least 30%. The emblicanin A content of this preparation was 10.2%.

Example 2

Toxicity Studies

Acute Toxicity

Healthy albino mice of either sex, having body weight 20-25 g were used. They were housed in clean polypropylene cages with food and water available ad libitum. After acclimatization for one week, their body weights were recorded and were divided into 8 groups of 6 each. Group A served as control and the remaining 7 groups were kept as experimental group. The experimental animals were supplied 200 mg, 400 mg, 600 mg, 800 mg, 2.5 g, 5 g and 10 g/kg of amla extract, respectively, orally after an overnight fasting. Animals were observed continuously for the first 6 h and mortality was recorded for 72 hours.

Amla extract up to a dosage level of 10 g/kg body weight produced no adverse effects such as increased motor activity, tremors, clonic convulsions, piloerection, muscle spasm, hyperesthesia, ataxia, sedation, hypnosis and analgesia. No mortality was recorded in 72 hours.

Sub Acute Toxicity

Thirty healthy male Sprague-Dawly rats weighing 200-250 g were used for the present study. They were housed in polypropylene cages (38×23×10 cms) with 5 animals per cage and maintained under standard housing conditions (room temperature 24-27° C. and humidity 60-65%) with 12-h light and dark cycle. The food in the form of dry pellets and water were available ad libitum.

The animal experiments were conducted according to internationally followed ethical standards and approved by the ethics committee of the Little Flower Hospital and Medical Research Centre, Angamaly, Kerala, India.

The animals were divided into 5 groups of 6 each. Group A served as control while groups B, C, D and E were fed orally a standardized extract of Emblica extract at dosages of 200 mg, 500 mg, 1.0 g and 2.0 g every day for 3 months. Body weights were recorded each week. At the end of 3 months blood samples were collected and analyzed for RBC, WBC, haemoglobin (Hb) and lymphocytes. Blood sugar, serum cholesterol, total protein, aminotransferases (SGOT, SGPT) and alkaline phosphatase were estimated by well-established standard methods. Cholesterol contents of liver and heart were estimated.

At the end of the study, all animals were sacrificed and the various organs and tissues were isolated for detailed examination. The main observations were:

1. All animals in the control and experimental groups showed a steady increase with weight and were in the normal range.
2. Haematological and biochemical parameters of both the control and experimental groups were in the normal range. The inventive extract was found to enhance the RBC, WBC counts and haemoglobin in the experimental group to a moderate degree. Three months of treatment produced a decrease in blood sugar, serum cholesterol as well as cholesterol in the heart and liver and a moderate increase in serum total protein.
3. Levels of the enzymes SGOT, SGPT and ALP were in the normal range indicating amla extract had no hepatotoxic effect.
4. There was a significant decrease in the HMG CoA reductase activity in the experimental group in a dose-dependent manner.
5. The lumen of aorta, myocardial cells, nephrotic tissues, hepatocytes, spleen tissue and tissues of the adrenal gland appeared normal on microscopic examination.
6. Oral feeding of amla extract up to a dose of 2 g/kg for 3 months does not produce any toxic effect.

Example 3

Male NZ white rabbits weighing 1.3-1.6 kg were individually caged and fed a normal standard diet. After an acclimatization period, they were divided into 4 groups of 5 animals each. One group (Group A) served as control and groups B1, B2 and B3 served as experimental groups. The experimental groups were made hypercholesterolemic by feeding 100 mg cholesterol along with the diet daily for 4 months. After 4 months, Group B1 was kept as untreated hypercholesterolemic control and the remaining two groups (B2 and B3) were fed orally with amla extract in the dosage of 10 mg and 20 mg/kg/day, respectively, for additional 4 months. Body weights of animals were recorded every 15 days.

Before starting the experiment, fasting blood was collected from all animals for estimation of serum total cholesterol, LDL cholesterol (LDL-C), HDL cholesterol (HDL-C) and triglycerides (TG). Blood samples were also analyzed for haematological parameters (RBC, WBC, haemoglobin (Hb) and lymphocytes). These analyses were repeated every month.

At the end of 8 months, all animals were sacrificed and liver, aorta, spleen, heart, liver and kidney were isolated and examined for gross macroscopic changes and thereafter fixed in 10% formalin for histological studies. Tissue cholesterol of liver, kidney, spleen and heart were estimated. A part of the liver was homogenized for estimating HMG CoA reductase and mevalonate.

One-way ANOVA with repeated measures was used to statistically analyze the variance over a period of time. Inter-group comparisons were also made using the same method. Punnet multiple comparison test was used to compare the baseline values with periodically observed values. Post ANOVA comparison in inter-group analyses was performed by using Turkey-Kramer multiple comparison test. Paired t-test was used to compare the biochemical parameters both before and after the experiment. The results are given in the following Tables (1-6).

TABLE 1

Haematological and Biochemical Parameters

| Parameters | Group A (Control) | Group B1 (Hyper-cholesterolemic control) | Group B2 | Group B3 |
|---|---|---|---|---|
| RBC (millions/mm$^2$) | 5.57 ± 0.27 | 5.63 ± 0.25 | 5.67 ± 0.21 | 5.68 ± 0.17 |
| WBC ('000/mm$^2$) | 7.63 ± 0.45 | 7.2 ± 0.1 | 7.66 ± 0.21 | 7.57 ± 0.32 |
| Lymphocytes ('000/mm$^2$) | 2.44 ± 0.33 | 2.17 ± 0.08 | 2.27 ± 0.04 | 2.61 ± 0.23 |
| Hb (g/dl) | 14.6 ± 1.21 | 13.59 ± 1.0 | 15.56 ± 1.23 | 14.4 ± 1.11 |
| Blood sugar (mg/dl) | 110.6 ± 6.50 | 118.83 ± 4.75 | 102 ± 4.0 | 104 ± 4.0 |
| Total protein (g/dl) | 5.56 ± 0.77 | 5.63 ± 0.40 | 5.73 ± 0.30 | 6.2 ± 0.2 |
| Liver-Chol. (mg/g) | 9.43 ± 0.20 | 14.63 ± 0.51* | 9.53 ± 0.10** | 9.56 ± 0.18** |
| Heart-Chol. (mg/g) | 7.31 ± 0.07 | 8.51 ± 0.20* | 7.50 ± 0.10** | 7.43 ± 0.10** |
| Kidney-Chol. (mg/g) | 5.58 ± 0.10 | 6.6 ± 0.18* | 5.56 ± 0.08** | 5.67 ± 0.01** |
| Spleen-Chol. (mg/g) | 3.40 ± 0.10 | 3.80 ± 0.12 | 3.42 ± 0.02 | 3.32 ± 0.05 |
| HMG CoA to Mevalonate ratio | 1.03 ± 0.15 | 0.90 ± 0.2 | 1.53 ± 0.6** | 1.33 ± 0.06** |

*significant increase (P < 0.05)
**Significant decrease (P < 0.05)

TABLE 2

Serum Cholesterol

| | Serum Cholesterol concentration (mg/dl) | | | | | |
|---|---|---|---|---|---|---|
| Group | 0 Month | 4 Month | 5 Month | 6 Month | 7 Month | 8 Month |
| A | 55.8 ± 5.0 | 56.66 ± 2.7 | 53.38 ± 3.25 | 53.33 ± 3.3 | 54.23 ± 0.9 | 52.8 ± 1.8 |
| B1 | 50 ± 2.72 | 229.16 ± 3.2 | 220.33 ± 2.8 | 200.83 ± 3.2 | 185.31 ± 1.9 | 164.28 ± 3.6 |
| B2 | 48.33 ± 4.3 | 228.13 ± 1.9 | 163.56 ± 5.8 | 88.89 ± 5.1 | 74.57 ± 3.4 | 63.33 ± 2.89 |
| B3 | 52.49 ± 3.2 | 230.83 ± 3.2 | 177.96 ± 4.4 | 95.0 ± 1.9 | 72.88 ± 2.0 | 58.33 ± 2.89 |

TABLE 3

LDL Cholesterol

| | Serum LDL Cholesterol (mg/dl) | | | | | |
|---|---|---|---|---|---|---|
| Group | 0 Month | 4 Month | 5 Month | 6 Month | 7 Month | 8 Month |
| A | 39.22 ± 4.91 | 39.72 ± 2.59 | 38.6 ± 5.82 | 36.51 ± 4.09 | 37.64 ± 0.53 | 36.62 ± 1.56 |
| B1 | 32.38 ± 1.80 | 195.73 ± 4.2 | 187.36 ± 1.8 | 169.79 ± 3.6 | 154.1 ± 3.2 | 136.22 ± 4.3 |

TABLE 3-continued

LDL Cholesterol

Serum LDL Cholesterol (mg/dl)

| Group | 0 Month | 4 Month | 5 Month | 6 Month | 7 Month | 8 Month |
|---|---|---|---|---|---|---|
| B2 | 32.4 ± 4.68 | 193.7 ± 2.2 | 137.5 ± 5.2 | 67.54 ± 5.61 | 54.26 ± 2.71 | 43.03 ± 2.27 |
| B3 | 33.57 ± 3.35 | 195.86 ± 2.4 | 153.76 ± 5.2 | 73.82 ± 2.90 | 53.41 ± 1.43 | 39.25 ± 2.12 |

TABLE 4

VLDL Cholesterol

Serum VLDL Cholesterol (mg/dl)

| Group | 0 Month | 4 Month | 5 Month | 6 Month | 7 Month | 8 Month |
|---|---|---|---|---|---|---|
| A | 8.28 ± 0.76 | 8.43 ± 0.75 | 8.08 ± 0.44 | 8.27 ± 0.46 | 7.95 ± 0.44 | 7.95 ± 0.44 |
| B1 | 8.96 ± 0.45 | 26.94 ± 0.89 | 25.19 ± 1.16 | 22.3 ± 1.09 | 20.26 ± 1.14 | 19.73 ± 0.9 |
| B2 | 8.79 ± 0.45 | 26.56 ± 0.77 | 17.69 ± 1.41 | 12.53 ± 0.46 | 10.25 ± 0.4 | 9.07 ± 0.46 |
| B3 | 8.96 ± 0.45 | 26.36 ± 0.79 | 17.12 ± 0.97 | 12.2 ± 0.40 | 9.42 ± 0.39 | 8.53 ± 0.46 |

TABLE 5

HDL Cholesterol

Serum HDL Cholesterol (mg/dl)

| Group | 0 Month | 4 Month | 5 Month | 6 Month | 7 Month | 8 Month |
|---|---|---|---|---|---|---|
| A | 8.33 ± 0.43 | 8.47 ± 0 | 8.19 ± 0 | 8.33 ± 0.45 | 8.33 ± 0.12 | 8.24 ± 0.08 |
| B1 | 8.75 ± 0.83 | 9.32 ± 0.98 | 7.78 ± 0.82 | 8.75 ± 0.84 | 8.94 ± 1.06 | 8.33 ± 0.13 |
| B2 | 8.81 ± 1.42 | 8.05 ± 0.85 | 8.19 ± 0 | 8.89 ± 0.96 | 10.05 ± 1.76 | 11.24 ± 1.07 |
| B3 | 8.81 ± 0.76 | 8.47 ± 1.20 | 8.61 ± 0.83 | 8.75 ± 0.84 | 10.05 ± 1.44 | 10.62 ± 1.07 |

TABLE 6

Serum Triglycerides

Serum Triglycerides (mg/dl)

| Group | 0 Month | 4 Month | 5 Month | 6 Month | 7 Month | 8 Month |
|---|---|---|---|---|---|---|
| A | 41.34 ± 3.85 | 42.15 ± 3.92 | 40.38 ± 2.22 | 41.33 ± 2.83 | 39.74 ± 2.72 | 39.74 ± 2.72 |
| B1 | 44.61 ± 2.11 | 134.84 ± 4.4 | 125.96 ± 5.8 | 111.53 ± 5.4 | 121.94 ± 4.3 | 98.67 ± 4.62 |
| B2 | 43.84 ± 0.61 | 133.33 ± 2.1 | 88.47 ± 2.15 | 62.67 ± 2.31 | 51.28 ± 2.22 | 45.33 ± 2.3 |
| B3 | 44.61 ± 2.1 | 132.55 ± 3.3 | 88.57 ± 4.84 | 61.0 ± 2.2 | 47.11 ± 1.93 | 42.67 ± 2.3 |

Results in the above tables reveal the dramatic effect of feeding amla extract on the lipid profiles of hypercholesterolemic animals. All the parameters returned almost to their original levels after 4 months of amla treatment. This unprecedented result strongly suggests that with continued treatment hypercholesterolemia could be completely reversed, at least in experimental animals.

This reversal of hypercholesterolemia was further supported by the results of histological examination of the aorta of the animals. Aortic strips of control groups were normal with normal intima, media and adventia. So was the case with those of amla-treated hypercholesterolemic rabbits, while there were smooth muscle cell proliferation, fatty infiltration and foam cell formation in the untreated hypercholesterolemic animals. Hepatocytes of all animals appeared normal.

Reduced HMG CoA reductase activity was noted in the amla extract-treated groups (data not shown). The activity of this key enzyme was reduced by 30 and 56%, respectively, in animals of Group B2 and B3.

Example 4

Human Study 1

Hypercholesterolemic subjects (total cholesterol >240 mg/dl, LDL Cholesterol >130 mg/dl) of either sex were selected for the study. Patients having valvular heart disease, congestive heart disease and diabetes and patients taking lipid lowering drugs were excluded from the study. A total of 70 patients were enrolled. They were divided into control group (20 patients) and intervention group (50). They were briefed about the study and written consents were taken before commencement of the study. Before commencement of the study blood samples were collected from each patient. The intervention group were advised to take amla extract in the form of 500 mg hard gelatin capsules in the dosage of 2-0-2 after meals. The study period was 3 months. Lipid profiles were determined at the end of each month. Results are given in Tables 7 and 8, shown in FIGS. 1 and 2.

Example 5

Human Study 2

Twenty two apparently healthy human volunteers aged 26 to 76 years consumed 500 mg of amla product, referred to as Amlamax, per day. None of the participants had a history of myocardial infarction, stroke or coronary revascularization. Their physical attributes such as height, weight and blood parameters were analyzed before study and 3 months after consumption of AmlaMax. These data are given in Table 9. The participants were arbitrarily divided into three groups, namely those between ages 26 to 45, 46 to 60 and those above 60 years. Response to Amlamax with respect to the studied parameters were impressive (Table 10), with only one non-responder each for total cholesterol and LDL cholesterol. There were two non-responders to fasting blood sugar reduction, three did not respond to TG and CRP while 5 persons did not show the expected increase in their HDL profiles. The extent of response among responders (Table 11) were as follows:

Total cholesterol: (−) 4.6 to 32.3% ↓ (mean 13.6%)
LDL cholesterol: (−) 4.9 to 41.9% ↓ (mean 17.4%)
HDL Cholesterol: (+) 2.2 to 44.8% ↑ (mean 15.8%)
Triglycerides (TG): (−) 1.4 to 62.9% ↓ (mean 27.2%)
CRP: (−) 4.2 to 65.0% ↓ (mean 48.1%)
FBS: (−) 1.1 to 28.5% ↓ (mean 10.8%)

The magnitude of change generally follows the extent of abnormality in the respective starting values. For example there were two participants with very high TG levels of 534 and 350, respectively. These two persons showed a decrease of 50.4% and 62.9%, respectively, after AmlaMax treatment. Similarly the patient showing the highest enhancement of 44.8% in HDL cholesterol had the lowest HDL cholesterol to start with. The most significant changes were noted in CRP levels which responded to AmlaMax very well. Here again the person who responded the maximum (88.4% reduction) had the highest starting CRP value of 12.0 which was reduced by AmlaMax treatment to the normal range of 1.4 mg/L. These results should be considered significant because such gross abnormalities are normally difficult to correct by drug treatment. The results on fasting blood sugar (FBS) are also noteworthy. FBS recorded the least mean changes in the participants, because most of them had near-normal FBS values. There was only one diabetic patient (FBS above 140 mg/dl (entry No. 1) (Tables 9 and 11)). This patient also recorded the highest reduction in FBS. AmlaMax did not produce random reduction in blood sugar irrespective of the starting value (as would a normal drug do) but only in those cases where such a correction is needed and thus does not lead to hypoglycemia, a problem observed with many drugs for hyperglycemia. One is reminded of one of the three attributes of an 'adaptogen' (Rasayana in Ayurveda): It must cause only minimal disorders in the body's physiological functions. In other words, AmlaMax corrects only where correction is required, rightly justifying its position as an adaptogen, and in sharp contrast with common medications.

In agreement with the above observation, AmlaMax also modulated thyroid function, correcting both hyper- as well as hypothyroidisms. Among the 22 participants involved in the study, there were two persons (one male and one female) with overt hypothyroidism with TSH levels of 79.96 and 111.02 mU/L. These values after 3 months of AmlaMax treatment were 38.96 and 76.79 mU/L, respectively and are expected to improve further to normal values on continued treatment. Similarly, there was one woman patient with overt hyperthyroidism with TSH level less than 0.01 mU/L which got corrected to normal level (1.32 mU/L) after 3 months of AmlaMax consumption. These results indicate the normalizing effect of AmlaMax on thyroid functions in patients with such disorders.

TABLE 9

Effect of the amla product on Lipid profile, CRP and FBS in Healthy Human Volunteers

| Group | Lipid Profile | | | | | | | | | | CRP (mg/l) | | FBS (mg/dl) | |
|---|---|---|---|---|---|---|---|---|---|---|---|---|---|---|
| | Chol | | TG | | VLDL | | LDL | | HDL | | | | | |
| | 0 Mo | 3 Mo | 0 Mo | 3 Mo | 0 Mo | 3 Mo | 0 Mo | 3 Mo | 0 Mo | 3 Mo | 0 Mo | 3 Mo | 0 Mo | 3 Mo |
| A | 235 | 200 | 229 | 190 | 46 | 38 | 151 | 125 | 38 | 37 | 2.4 | 2.3 | 225 | 162 |
| (Age | 275 | 188 | 534 | 265 | — | 53 | — | 93 | 29 | 42 | 1.6 | 2.0 | 125 | 94 |
| 25-45 Yr) | 310 | 276 | 192 | 170 | 38 | 34 | 238 | 204 | 34 | 38 | 4.0 | 4.5 | 74 | 71 |
| (n = 13) | 230 | 211 | 167 | 110 | 33 | 22 | 156 | 147 | 41 | 42 | 3.5 | 2.8 | 85 | 76 |
| | 230 | 212 | 158 | 150 | 32 | 30 | 157 | 142 | 41 | 40 | 2.8 | 1.0 | 100 | 94 |
| | 270 | 212 | 250 | 250 | 50 | 50 | 173 | 124 | 38 | 47 | 3.8 | 2.5 | 95 | 94 |
| | 220 | 165 | 196 | 130 | 39 | 26 | 147 | 100 | 34 | 39 | 1.9 | 2.1 | 80 | 76 |
| | 240 | 229 | 273 | 180 | 55 | 36 | 147 | 150 | 38 | 43 | 2.0 | 3.2 | 95 | 100 |
| | 235 | 212 | 294 | 185 | 59 | 37 | 142 | 135 | 34 | 40 | 3.0 | 1.5 | 92 | 76 |
| | 220 | 176 | 142 | 130 | 28 | 26 | 136 | 99 | 51 | 56 | 4.0 | 1.9 | 93 | 82 |
| | 235 | 212 | 350 | 130 | 70 | 26 | 121 | 147 | 39 | 44 | 3.0 | 1.3 | 110 | 97 |
| | 245 | 224 | 175 | 175 | 35 | 35 | 172 | 147 | 38 | 42 | 2.6 | 1.1 | 85 | 82 |
| | 260 | 176 | 158 | 120 | 32 | 24 | 184 | 107 | 44 | 45 | 12 | 1.4 | 102 | 76 |
| Group B | 210 | 188 | 92 | 70 | 18 | 14 | 144 | 126 | 48 | 48 | 4 | 1.4 | 108 | 147 |
| (Age | 275 | 241 | 271 | 210 | 54 | 42 | 180 | 159 | 41 | 40 | 2 | 1.6 | 95 | 88 |
| 45-60 Yr) | 180 | 152 | 192 | 120 | 38 | 24 | 92 | 86 | 42 | 50 | 3.8 | 2.4 | 75 | 71 |
| (n = 6) | 245 | 224 | 100 | 90 | 20 | 18 | 175 | 164 | 40 | 46 | 3.0 | 2.9 | 95 | 82 |
| | 285 | 253 | 142 | 140 | 28 | 28 | 219 | 182 | 38 | 43 | 4.5 | 1.8 | 100 | 88 |
| | 235 | 259 | 273 | 200 | 55 | 40 | 142 | 181 | 38 | 38 | 4.2 | 1.0 | 98 | 97 |

TABLE 9-continued

Effect of the amla product on Lipid profile, CRP and FBS in Healthy Human Volunteers

| Group | Lipid Profile | | | | | | | | | | CRP (mg/l) | | FBS (mg/dl) | |
|---|---|---|---|---|---|---|---|---|---|---|---|---|---|---|
| | Chol | | TG | | VLDL | | LDL | | HDL | | | | | |
| | 0 Mo | 3 Mo | 0 Mo | 3 Mo | 0 Mo | 3 Mo | 0 Mo | 3 Mo | 0 Mo | 3 Mo | 0 Mo | 3 Mo | 0 Mo | 3 Mo |
| Group C (Age >60 Yr) (n = 4) | 220 | 153 | 117 | 80 | 23 | 16 | 163 | 90 | 34 | 47 | 4.0 | 1.2 | 95 | 88 |
| | 220 | 200 | 242 | 250 | 48 | 50 | 138 | 110 | 34 | 40 | 3.7 | 1.9 | 90 | 88 |
| | 245 | 224 | 167 | 100 | 33 | 20 | 174 | 165 | 38 | 39 | 2.9 | 1.2 | 125 | 109 |

Chol = Total cholesterol;
VLDL = very low density lipoproteins;
LDL = low density lipoproteins;
HDL = high density lipoproteins;
TG = Triglyceride;
CRP = C-reactive protein;
FBS = Fasting blood sugar;
Mo = Months after treatment with AmlaMax

TABLE 10

Response of Healthy Subjects to Treatment with the product

| Parameter | No of Non-responders |
|---|---|
| Cholesterol | 1 (4.5%) |
| LDL chol | 1 (4.5%) |
| HDL chol | 5 (22.7%) |
| TG | 3 (13.6%) |
| CRP | 4 (18.18%) |
| FBS | 2 (9.1%) |

Total number of subjects treated = 22

TABLE 11

Extent of Response to Treatment with the product in Healthy Human Subjects

| Subject | Cholesterol | Triglycerides | LDL cholesterol | HDL cholesterol | C-reactive protein | Fasting blood sugar |
|---|---|---|---|---|---|---|
| 1 | −15% | −18.0% | −27.2% | −2.6% | −4.2% | −28.0% |
| 2 | −31.6 | −50.4 | — | +44.8 | +11.1 | −24.8 |
| 3 | −11 | −11.5 | −14.3 | +11.7 | +12.5 | −4.1 |
| 4 | −8.3 | −34.2 | −5.8 | +2.4 | −20.0 | −10.6 |
| 5 | −8.3 | −5.1 | −9.6 | −2.5 | −64.3 | −6.0 |
| 6 | −21.5 | 0.0 | −28.4 | +23.6 | −34.3 | −1.1 |
| 7 | −25.0 | −33.7 | −32.0 | +14.7 | +10.5 | −5.0 |
| 8 | −4.6 | −36.1 | +2.0 | +13.1 | +60.0 | +5.2 |
| 9 | −9.8 | −36.9 | −4.9 | +17.6 | −50.0 | −17.4 |
| 10 | −20.0 | −8.5 | −27.2 | +9.8 | −52.5 | −11.9 |
| 11 | −9.8 | −62.9 | +21.5 | +12.8 | −56.7 | −11.9 |
| 12 | −8.6 | 0.0 | −15.5 | +10.5 | −57.3 | −3.6 |
| 13 | −32.3 | −24.1 | −41.9 | +2.2 | −88.4 | −25.5 |
| 14 | −10.5 | −24.0 | −12.5 | 0.0 | −65.0 | +38.6 |
| 15 | −12.4 | −23.4 | −11.7 | −2.5 | −20.0 | −7.4 |
| 16 | −15.6 | −37.5 | −6.6 | +19.0 | −35.9 | −5.4 |
| 17 | −8.6 | −10.0 | −16.9 | +15.0 | −4.4 | −13.7 |
| 18 | −11.3 | −1.4 | −6.3 | +13.1 | −60.0 | −12.0 |
| 19 | +10.2 | −26.8 | +27.4 | 0.0 | −76.2 | −1.1 |
| 20 | −30.5 | −31.7 | −44.8 | +38.2 | −70.0 | −7.4 |
| 21 | −9.1 | +5.4 | −20.3 | +17.6 | −48.7 | −2.3 |
| 22 | −8.6 | −40.2 | −5.2 | +2.6 | −58.7 | −12.8 |
| Mean Change* | (−)13.6 | (−)27.2 | (−)17.4 | (+)15.8 | (−)48.1 | (−)10.8 |

*Among responders

The foregoing embodiment and advantages are merely exemplary and are not to be construed as limiting the present invention. The present teaching can be readily applied to other types of apparatuses. Also, the description of the embodiments of the present invention is intended to be illustrative, and not to limit the scope of the claims, and many alternatives, modifications, and variations will be apparent to those skilled in the art.

I claim:

1. A method of reducing HMG CoA reductase activity comprising administering effective doses of an extract of *Emblica officinalis* to a subject in need thereof, the extract prepared by a method comprising:
   pulping fruits of *Emblica officinalis* with demineralized water to create a slurry;
   treating the slurry with pectinase;
   filtering the slurry to create a solution; and
   concentrating the solution to generate the extract of *Emblica officinalis*.

2. A method for increasing ratio of HMG CoA to mevalonate comprising administering effective doses of an extract of *Emblica officinalis* to a subject in need thereof, the extract prepared by a method comprising:
   pulping fruits of *Emblica officinalis* with demineralized water to create a slurry;
   treating the slurry with pectinase;
   filtering the slurry to create a solution; and
   concentrating the solution to generate the extract of *Emblica officinalis*.

* * * * *